United States Patent
Sandal et al.

(10) Patent No.: US 6,723,504 B1
(45) Date of Patent: Apr. 20, 2004

(54) METHOD FOR GENERATING A GENE LIBRARY

(75) Inventors: Thomas Sandal, Herlev (DK); Carsten Sjøholm, Allerød (DK); Thomas Schäfer, Farum (DK); Lene Lange, Valby (DK); Fiona Duffner, Copenhagen (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/426,340

(22) Filed: Oct. 25, 1999

Related U.S. Application Data

(60) Provisional application No. 60/106,319, filed on Oct. 30, 1998.

(30) Foreign Application Priority Data

Oct. 28, 1998 (DK) .......................................... 1998 01388

(51) Int. Cl.[7] .............................. C12Q 1/68; C12Q 1/02; C12P 19/34; C12N 15/64
(52) U.S. Cl. ............................ 435/6; 435/29; 435/91.1; 435/91.41; 435/91.5
(58) Field of Search ............................. 435/6, 29, 91.1, 435/91.41, 91.5, 320.1; 536/23.1, 23.2, 23.7

(56) References Cited

U.S. PATENT DOCUMENTS

| | | | |
|---|---|---|---|
| 4,027,037 A | * 5/1977 | Siegle et al. ................ | 424/314 |
| 5,763,239 A | 6/1998 | Short et al. ............... | 435/172.1 |

FOREIGN PATENT DOCUMENTS

| | | | |
|---|---|---|---|
| WO | WO 93/11249 | | 6/1993 |
| WO | 96/06175 | * | 2/1996 |
| WO | WO 97/37036 | | 10/1997 |

OTHER PUBLICATIONS

Sarkar, A. and Upadhyay, S.N. Folia Microbiologica 38(1):29–32, 1993.*
Cotta, M.A. Appl. Environ. Microbiol. 54(3):772–6, Mar. 1988.*
Jacobsen, R.L. and Schlein, Y. J. Euk. Microbiol. 44(3):216–219, Jun. 1997.*
Okuta et al., (1998) Gene 212:221–228.
Prescott, L.M. (1993) Microbiology 2nd ed. Wm. C. Brown Publishers, Dubuque, IA. pp. 251–252.

* cited by examiner

Primary Examiner—Carla J. Myers
Assistant Examiner—Diana B. Johannsen
(74) Attorney, Agent, or Firm—Elias Lambiris; Jason Garbell

(57) ABSTRACT

The present invention relates to a method of generating a gene library from an environmental pool of organisms, which gene library is enriched in DNA encoding a polypeptide with an activity of interest. Also, the invention provides a method of selecting a DNA sequence of interest from an environmental pool of organisms. Further, the invention relates to a gene library prepared from an enriched environmental pool of organisms enriched in DNA encoding a polypeptide with an activity of interest.

23 Claims, No Drawings

METHOD FOR GENERATING A GENE LIBRARY

CROSS-REFERENCE TO RELATED APPLICATIONS

This application claims priority under 35 U.S.C. 119 of Danish application PA 1998 01388 filed Oct. 28, 1998 and of U.S. provisional No. 60/106,319, filed Oct. 30, 1998, the contents of which are fully incorporated herein by reference.

TECHNICAL FIELD

The present invention relates to a method of generating a gene library from an environmental pool of organisms, which gene library is enriched in DNA encoding a polypeptide with an activity of interest.

BACKGROUND OF THE INVENTION

The advent of recombinant DNA techniques has made it possible to select single protein components with interesting properties and produce them on a large scale. This represents an improvement over the previously employed production process using microorganisms isolated from nature and producing a mixture of proteins which would either be used as such or separated after the production step. Methods have been developed for rapid identification of genes encoding a polypeptide of interest.

One example is the so called expression cloning technique described in WO 93/11249 (Novo Nordisk A/S). The technique disclosed in WO 93/11249 comprises a method of screening for a DNA sequence in a DNA library prepared from an organism suspected of producing genes encoding polypeptides with activities of interest. Such a library has traditionally been made on DNA isolated from a single known microorganism.

A compartmentalization method of screening microorganisms having a selectable characteristic has previously been devised in WO 97/37036, and a process for forming a normalized genomic DNA library from an environmental sample is described in WO 97/37036.

However, a method of generating a gene library from an environmental pool of organisms, which gene library is enriched in DNA encoding a polypeptide with an activity of interest has never been described. Therefore, it would be desirable to have a method based on biological enrichment for selecting potentially interesting genes from environmental pool of organisms.

SUMMARY OF THE INVENTION

It has now been found possible to use biological enrichment for selecting potentially interesting genes from an environmental pool of organisms. Accordingly, the invention provides a method for generating a gene library from an environmental pool of organisms, which gene library is enriched in DNA encoding a polypeptide with an activity of interest, which method comprises:

a) subjecting the environmental pool of organisms to cultivation in a medium and/or under conditions suitable for enriching said pool of organisms in organisms harbouring said DNA; and b) preparing a gene library from the resulting enriched pool of organisms.

The invention also provides a method of selecting a DNA sequence of interest from an environmental pool of organisms, which method comprises:

a) subjecting the environmental pool of organisms to cultivation in a medium and/or conditions suitable for enriching said pool of organisms in organisms harbouring said DNA sequence;

b) producing gene libraries from the resulting enriched pool of organisms;

c) screening the libraries for DNA containing the desired gene; and d) selecting the DNA sequence of interest resulting from the screening of step c).

Further, the invention relates to a gene library prepared from an enriched environmental pool of organisms enriched in DNA encoding a polypeptide with an activity of interest.

DETAILED DISCLOSURE OF THE INVENTION

It is an object of the present invention to provide a method for generating a gene library from an environmental pool of organisms, which gene library is enriched in DNA encoding a polypeptide with an activity of interest, which method comprises:

a) subjecting the environmental pool of organisms to cultivation in a medium and/or under conditions suitable for enriching said pool of organisms in organisms harbouring said DNA; and b) preparing a gene library from the resulting enriched pool of organisms.

In the context of the present invention, the term "an environmental pool of organisms" means a environmental sample comprising microorganisms and cells from higher animals harboring DNA encoding a polypeptide with an activity of interest. The environmental sample may for instance be an environmental sample of soil or plant material, animal or insect dung, insect gut, animal stomach, a marine sample of sea or lake water, sewage, waste water, a sample of sludge or sediment, etc., comprising one or, as in most case, a vast number of different microorganisms or living cells.

In step a), the sample as such is cultivated without any need for further purification. By selecting the medium and the cultivation conditions at which the sample is cultivated, it is possible for enriching or (amplifying) organisms having optimal growth at the specific cultivation conditions, and expressing polypeptides with properties adapted to the cultivation conditions. The gene library prepared in step b) may be prepared by any suitable technique known in the art, non-limiting examples of which are described in Example 3 and 4.

The advantage presented by the present screening method is primarily that the rate at which novel genes may be isolated and, consequently, novel products be developed may be greatly increased. Furthermore, the method permits screening for multiple polypeptides activities and may even result in the isolation of several different genes coding for the same type of polypeptides.

By use of the invention it is possible to exploit enriched cultures for detecting novel enzymes, and other polypeptides with an activity of interest.

In a preferred embodiment, the method of the invention comprises subjection the environmental pool of organisms to cultivation in a medium, which contains a substrate for the polypeptide with the desired activity. A wide range of substrates for the enrichment of the environmental of organisms containing different types of gene products may be used. For instance, a DNA encoding a polypeptide with an activity of interest such as a pectinase enzyme may be selected as a gene product on a substrate as pectin.

In a preferred embodiment, the substrate constitutes the carbon source and/or nitrogen source of the medium.

In a more preferred embodiment, the substrate comprises pectin, amylose, cellulose, galactan, xylan, arabinan, mannan, lipid or hemicellulose or a combination thereof.

In a preferred embodiment of the method of the invention, the enrichment is achieved by one or more growth conditions. In a another preferred embodiment, the growth conditions comprise pH and temperature. In yet another preferred embodiment, the growth conditions of step a) used for achieving the enrichment comprises any pH range ie. 0–12, preferably of about 6–9, in particular 9–12, at any temperature range i.e. 0–120° C., preferably about 25–30°, preferably 30–500°, most preferred 50–70° C.

An important step in the procedure for selection of a potentially interesting environmental pool of organisms is to select the optimal pool to start from. To select genes encoding polypeptides that can break down natural compounds of plant (or animal) origin, it is preferable to look into those biotopes in nature where such materials are efficiently decomposed. Examples of animals especially efficient in breaking down plant material are the ruminates, termites and insects (sensu lato).

In a preferred embodiment, the environmental pool of microorganisms is isolated from an animal stomach or an insect gut.

In a more preferred embodiment, the pool of microorganisms is isolated from a cow's rumen.

Likewise, it is important when selecting genes encoding polypeptides with an activity of interest that are capable of working under e.g. strongly alkaline conditions, to isolate the pool of organisms from an equally strongly alkaline biotope. It is known in the art that in order for *Bacillus thuringensis* (*Bt*) toxins to be active, strongly alkaline conditions are a prerequisite [*Bacillus thuringensis*, an environmental biopesticide: Theory and Practice, 1993, eds. P. F. Entwistl et al., Wiley & Son, UK]. The guts of the larvae belonging to the orders of insects known to be sensitive to the *Bt* toxins comprise environmental pools of a high alkaline nature (approx pH 10). Such insect orders are especially Isoptera, Lepidoptera, Coleoptera and Diptera.

Consequently in a preferred embodiment, the pool of microorganisms is isolated from the gut of an insect of the Isoptera, Lepidoptera, Coleoptera, or Diptera families.

In a more preferred embodiment, the pool of microorganisms is isolated from the gut of insects selected from the group consisting of Agrotis, *Neotermes castaneus, Tineola bisselliella*, and *Melolontha vulgaris.*

Prior to isolating environmental pools of organisms from animal stomachs or insect guts, it is interesting to do an enrichment by rearing or supplying the animal or insect with food comprising a substrate for the activity of the polypeptide of interest, maybe even as the primary carbon and/or nitrogen source. This makes a cow's rumen and larval guts from Lepidopteran, Coleopteran and Dipteran species highly interesting for further enrichment through feeding with specific substrates.

In a preferred embodiment the pool of microorganisms is enriched by supplying feed to the animal or insect, which comprises a substrate for the polypeptide with an activity of interest.

Specific examples of "DNA encoding a polypeptide with an activity of interest" include among others enzymatic activity and anti-microbial activity.

In a preferred embodiment, the gene libraries are enriched in DNA encoding an enzyme activity of interest.

In a more preferred embodiment of the invention the activity of interest is an enzymatic activity, such as an activity selected from the group comprising of phosphatases oxidoreductases (E.C. 1), transferases (E.C. 2); hydrolases (E.C. 3), such as esterases (E.C. 3.1), in particular lipases and phytase; such as glucosidases (E.C. 3.2), in particular xylanase, cellulases, hemicellulases, and amylase, such as peptidases (E.C. 3.4), in particular proteases; lyases (E.C. 4); isomerases (E.C. 5); ligases (E.C. 6).

In another preferred embodiment, the enzyme of interest comprises a protease, lipase, beta-galactosidase, lactase, polygalacturonase, beta-glucoamylase, esterase, hemicellulase, peroxidasee, oxidase, laccase or glucose oxidase.

In more preferred embodiment, the enzymes obtained in the method is an amylase, in particular an α-amylase or a β-amylase, an arabinanase, an arabinofuranosidase, a galactanase, an α-galactosidase, a β-galactosidase, a polygalacturonase, a pectin methyl esterase, a rhamnogalacturonase, a rhamnogalacturon acetyl esterase, a pectin lyase, a xylanase, a cellulase, a β-glucosidase, a cellobiohydrolase, a xylosidase, a mannanase, and/or a glucuronisidase.

The environmental pool of organisms containing DNA encoding a polypeptide with an activity of interest are typically microorganisms such as Eubacteria, Archaebacteria, fungi, algae and/or protozoa.

The polypeptide may be an enzyme of interest obtained from any known organism. Preferably the enzyme may be obtained from microorganism, in particular from a bacteria, from a filamentous fungus or a yeast.

In the method of the invention, the organisms are enriched cultures meaning that the cultures are selected on a specific substrate from which other organisms are not able to grow or having a reduced growth.

It is another object of the invention to provide a method of selecting a DNA sequence of interest from an environmental pool of organisms, which method comprises:

a) subjecting the environmental pool of organisms to cultivation in a medium and/or conditions suitable for enriching said pool of organisms in organisms harbouring said DNA sequence;

b) producing gene libraries from the resulting enriched pool of organisms;

c) screening the libraries for DNA containing the desired gene; and d) selecting the DNA sequence of interest resulting from the screening of step c).

Step a) and b) are as described above. In step c), clones found to comprise a DNA sequence originated from the prepared gene library in step b) may be screened for any activity of interest. Examples of such activities include enzymatic activity, anti-microbial activity or biological activities. In step c), gene libraries are screened for genomic DNA containing the desired gene, and in step d), the DNA sequence of interest are selected from the screening of step c). Step c) and d) may be performed by standard methods known in the art.

The polypeptide with the activity of interest may then be tested for a desired performance under specific conditions and/or in combination with e.g. chemical compounds or agents. The gene libraries may be screened according to the method of the invention for a polypeptide with an activity of interest e.g. a specific activity, and/or a specific property of interest such as thermostability, high pH tolerance, wash performance, textile dyeing, hair dyeing or bleaching properties, a effect in feed or food ect. The appropriate assay for testing for a desired activity and/or property well be known to the skilled person.

In a preferred embodiment of the method, the gene library comprises an enzyme-encoding gene of interest, and the gene library is screened for enzymes under conditions which the enzyme is active. This means that the library may be screened for enzymes at e.g. high ,temperatures such as 60–110° C. and high pH such as 10–12 e.g. in cases where it is desired to isolate a DNA sequence encoding an alkaline enzyme with a relatively high thermostability. However, pH can be in any range e.g. of from about 0 to about 12, and the temperature in any range e.g. of from about 5 to about 110° C., preferably of from about 60 to about 90° C.

It is still another object of the invention to provide a gene library prepared from an environmental pool of organisms enriched in DNA encoding an polypeptide with an activity of interest. In a preferred embodiment, the gene library comprises a polypeptide with an activity of an enzyme, a hormone or a toxin. In a more preferred embodiment, the gene library comprises an enzyme activity of interest as described above.

The invention is further illustrated in the following examples which is not intended to be in any way limiting to the scope of the invention.

EXAMPLES

Example 1
Enrichment Procedure

Shake flasks with 100 ml of the respective media described below were inoculated with approximately 1 g of soil samples (NS Collection), and incubated at 60° C. overnight at 250 rpm. The pH in the shake flasks after incubation were 9.7 to 9.9. All enrichments were checked for growth by microscopy.

Media for enrichment were prepared by mixing of the 10 fold concentrated stock solutions below:

| A: | $KH_2PO_4$ | 4.25 g/l |
|---|---|---|
|  | $NH_4Cl$ | 4.25 g/l |
|  | KCl | 4.25 g/l |
|  | $MgSO_4$, $7H_2O$ | 6.25 g/l |
|  | $CaCl_2$, $2H_2O$ | 3.12 g/l |
| B: | $NaHCO_3$ | 30 g/l |
|  | $Na_2CO_3$ | 30 g/l |
| C: | Yeast extract | 5 g/l |
| Pectin | Pectin 35 | 20 g/l |
| Cellulose | CMC C-4888 Sigma | 10 g/l |
|  | Cellulose Powder | 20 g/l |
| Starch | Soluble starch | 50 g/l |
| Boiled before autoclaving |  |  |

All stock solutions were autoclaved.

The respective liquid enrichment media were prepared by mixing 100 ml of A+B+C+100 ml pectin or cellulose or starch and 600 ml sterile water.

Example 2
Enrichment Library Material

The enrichments were used for preparation of a mixed enrichment library. 50 ml of each selected enrichment culture were centrifuged and the combined cell pellets used for gene library construction. The clones were obtained by screening of the library, distributed on amylase, arabinase, xylanase, galactanase and pectinase activity.

Example 3
Preparation of Gene Library No. 1

The cells from the cultures were washed with 0.9% NaCl and pooled into one tube.

DNA was extracted using method described by Pitcher et al. (Pitcher, D. G., saunders, N. A., Owen; R. J. (1989). Rapid extraction of bacterial genomic DNA with guanidium thiocyanate. Lett.Appl.Microbiol., 8,151–156.). The DNA extraction recovered 170 µg high molecular weight DNA. Approximately 90 µg DNA in 25% glycerol were fragmented in a nebulizer (Bio Neb Cell Disruption System with an DNA insert, Glas-Col Apparatus Company) for 45 sec at a pressure of 15 PSI. This resulted in DNA from 2–5 Kb. The DNA was size-fractionated on a sucrose gradient (Maniatis et al.), and the fractions of interest were pooled and concentrated by EtOH or isopropanol precipitation. To trim the ends 4 µg DNA was EtOH precipitated and resuspended in 35 µl $H_2O$.

The DNA were trimmed to make blunt ends.

35 µl DNA (4 µg)
5 µl NEB4 buffer
4 µl dNTP (2.5 mM stock)
4 µl T4 DNA polymerase
2 µl Klenow The reaction mixture was incubated at room temp. for 30 min, and 200 µl 1×TE, pH 8.0, were added. The mixture was extracted with 1×phenol-chloroform, 1×CIA, 0.1 vols 3 M NaOAc was added, pH 5.2, 2 vols 96% EtOH were added, ppt on ice for 30 min, or overnight at −20° C. and resupended in 16 µl $H_2O$.

The end trimmed DNA was ligated into a fresh Eco RV digested pzero (Invitrogen).

The ligation mixture was transformed into DH10B E.coli cells by electroporation and frozen in aliqouts corresponding to 300 zeocin resistant colonies. The frozen alliqouts constitute the library no. 1.

Example 4
Isolation of Bacteria From Soil and Preparation of Gene Library No. 2

Bacterial isolation from soil was as described by Prieme, A. et al. and Bakken, L. R., (*FEMS Microbiology Ecology* 21:59–68, 1996). 50 g of soil (obtained from the Roskilde Fjord in Denmark) and 200 ml $dH_2O$ were blended for 1 min (Waring blender) and placed 1 min on ice. This was repeated 3 times. The suspension was left on the bench for 2 min to allow the large soil particles to settle. 30 ml of the suspension was added to a centrifuge tube followed by 10 ml Nycodenz* (*Nycodenz; 0.8 g/ml in $H_2O$, sterile filtered, Nycomed pharma A/S batch no. 207051) which was added via a syringe to the base of the tube. The samples were centrifuged with a swing-out rotor at 10,000×g for 2 h, no break, 20° C. The bacteria were collected in the interface between the Nycodenz and water phases (the soil remains were at the base of the tube) and were removed with a syringe.

DNA was extracted using the method described by Pitcher et al. (Pitcher, D. G., saunders, N. A., Owen; R. J. (1989). Rapid extraction of bacterial genomic DNA with guanidium thiocyanate. Lett.Appl.Microbiol., 8,151–156.).

The DNA was partially digested with the restriction enzyme Sau3A and the DNA was size-fractionated on a 1% agarose gel (Maniatis et al.). The agarose containing the DNA corresponding to 3 kb and upwards in size was cut from the agarose gel and the DNA was concentrated by further electrophoresis into a 1.2% agarose gel. The DNA was isolated from the agarose piece using the GFX kit (Pharmacia).

The Sau3A digested DNA was ligated into a fresh BamHI digested pzero-2 (Invitrogen). The ligation mixture was transformed into DH10B E.coli cells by electroporation and frozen in aliqouts corresponding to 300 kanamycin resistant colonies. The frozen aliqouts constitute the library no. 2.

Example 5

Assaying Gene Library No. 1 for Enzyme Activity

Amylame Assay

The assay contains the following reagents:

1: 0,1% AZCL Amylose (MegaZyme, Australia)
2: 0,1 M Tris-Cl buffer pH9
3: MilliQ H2O 96 well: In each well were 150 µl (~15 ml/microplate) used as standard volume.

384 well: In each well were 60 µl (~25 ml/microplate) used as standard volume.

The cells were grown for 65 hours, and thereafter 50 µl of cells were pipetted into 150 µl assay substrate for 96 well plates or 20 µl into 60 µl assay substrate for 384 well plates. The assay-plates were incubated over night at 500° C. in a bag. Positive reactions were observed as blue colour in the well.

Arabinase Assay

The assay contains the following reagents:

1: 0,1% AZCL—Debranched Arabinan(MegaZyme, Australia)
2: 0,1 M Tris-Cl buffer pH 9
3: MilliQ H2O 96 well: In each well were 150 µl used as standard volume.

384 well: In each well were 60 µl used as standard volume.

The cells were grown for 65 hours, and thereafter 50 µl of cells were pipetted into 150 µl assay substrate for 96 well plates or 20 µl into 60 µl assay substrate for 384 well plates. The assay-lates were incubated over night at 50° C. in a bag. Positive reactions were observed as blue colour in the well.

Galactanase Assay

The assay contains the following reagents:

1: 0,1% AZCL Galactan (MegaZyme, Australia)
2: 0,1 M Tris-Cl buffer pH9
3: MilliQ H2O 96 well: In each well were 150 µl used as standard volume.

384 well: In each well were 60 µl used as standard volume.

The cells were grown for 65 hours, and thereafter 50 µl of cells were pipetted into 150 µl assay substrate for 96 well plates or 20 µl into 60 µl assay substrate for 384 well plates. The assay-plates were incubated over night at 50° C. in a bag. Positive reactions were observed as blue colour in the well.

Pectinase Assay

Numbered black microtiter plates were filled with 150 ml assay mix* as described below using a Multidrop instrument. Subsequently, 50 ml of cells were pipetted automatically into the assay plates using a Plate Mate pipetting station. Plates were left at room temperature (in the dark) for approximately 150–180 min., and subsequently read by a FPM-2 fluorescence polarization reader using excitation-filter 485/22 and emission-filter 530/30. Positive clones were scored as a lowering of the polarization value which typically was from approximately 90 mP to 50–70 mP.

150 µl assay mix*
34 µg/ml Fluorescein-labelled lemon-pectin 77% DE = 5.0 µl 1 g/l solution
2 mM CaCl2 = 0.5 µl 1 M solution
83 vol. % 0.1 M glycin-buffer with 0.1 M NaCl = 125 µl buffer pH 10.0
Mili-Q-H2O = 20 µl Xylanase Assay The assay contains the following reagents:

1: 0,1% AZCL—Xylan(MegaZyme, Australia)
2: 0,1 M Tris-Cl buffer pH9
3:MilliQ H2O 96 well: In each well were 150 µl used as standard volume.

384 well: In each well were 60 µl used as standard volume.

The cells were grown for 65 hours, and thereafter 50 µl of cells were pipetted into 150 µl assay substrate for 96 well plates or 20 µl into 60 µl assay substrate for 384 well plates. The assay-plates were incubated over night at 50° C. in a bag. Positive reactions were observed as blue colour in the well.

Plate Screening Assay for Xyloglucanase, Galactanase and Amylase Containing E.coli Trannformants.

Gene Library no. 2 was screened on LB agar plates containing 25 µg/ml kanamycin as the antibiotic selection marker and 0.03% AZCL-xyloglucan+0.03% AZCL-galactan+0.03% AZCL-amylose as enzyme substrates at 37° C. The formation of a blue halo around the colony indicates enzyme activity. The colony was restreaked onto LB plates containing each of the AZCl substrates to identify the enzyme activity. Three amylase positive clones were discovered.

Positives Obtained From Library No. 1 by Screening With Above Described Assays.

Three amylase positive clones, two xylanase positive, two pectinase positive, two galactanase positive, and finally eight arabinase positive clones were discovered.

These results demonstrate that it is possible to select a DNA sequence of interest with the present method of the invention.

Example 6

Enrichment of Termite Larvae Gut for Cellulases

Materials: Termite larvae (*Neotermes castaneus*) were acquired from BAM (Bundesanstalt für Materialforschung und-Prüfung, Berlin, Germany).

Enrichment procedure: The larvae were subsequently reared and fed on non-sterile plant materials, originating either from gymnosperms or angiosperms (monocot or dicot), enabling enzymatic (endo- and exo-) digestion through plant cell wall degrading enzyme activity.

Further enrichment through dissection national: The larvae were decapitated under a stereoscopic microscope after which the guts (including gut content) were selected and pooled together from several animals.

DNA preparation: DNA preparations were made from such composite gut materials using commercially available DNA kits (FAST DNA-KitH, Bio 101 Inc, 1070 Joshua Way, Calif., US). This high quality DNA material was used to prepare a genomic library, e.g. following a protocol as follows: digestion by Sau3A, fractionation and selection of specific size range, cloning in the Bacteriphage Lambda-Zap-Express (AH Diagnostic, originating from Stratagenel US). Full protocols are given by the kit-manufacturers.

RNA preparation: Total RNA preparations were made from said composite gut materials using commercially available RNA kits and public protocols, as e.g. indicated in (H.Dalbøge, 1997, FEMS Microbiology Reviews 21, 29–42). The mRNA fraction was subsequently harvested. Based on this fraction, the corresponding cDNA prep was made. This was used to construct a cDNA library, representing the expressed proteins at the given time. Protocols and references for mRNA, cDNA and cDNA library construction are available in common textbooks (plus in e.g. H.Dalbøge, 1997, FEMS Microbiology Reviews 21: 29–42).

Screening of the genomic library enriched for DNA from those organisms that specifically benefitted from the feeding conditions of the larvae under preparation: A plaque screening procedure was adapted to function with enzyme substrate holding plates (e.g. prepared from the AZCL blue granule substrates, available from MegaZyme). Thus colourhalos indicated which phages were holding an inserted full functional gene, encoding an enzyme with the cellulase activity of interest. The procedure is most successful when the enzyme substrate is incorporated in a bottom layer and the phages are added in a separate layer on top. The positive plaques on the AZCL substrate plates could be detected by their blue halos.

Screening of the cDNA library enriched for high expression of proteins useful to degrade the feed given to the larvae was performed according to the protocol for expression cloning, as given in H.Dalbøge, 1997 (FEMS Microbiology Reviews 21: 29–42).

Identified hits: more than 200 cellulase active clones were finally identified on HE Azur cross linked blue granule substrates from MegaZyme. PCR made directly from individual colonies (PCR procedures as indicated in relevant text books, using e.g. the polymerases available from Advanced Biotechnologies, Surrey, UK) was used to differentiate and group the hits. The primers used were based on recognition and amplification of the sense and antisense cDNA cloning plasmid pYes-2 (commercially available from Invitrogene, US).

At least four different sized functional genes were hereby identified.

Example 7
Enrichment of Textile Moth Larvae Gut for Proteases

Materials: Larvae of *Tineola bisselliella*, the lepidopteran textile moth were acquired from BaM in Germany. Standard protocols are referred in Example 6.

Enrichment procedure: The larvae were subsequently reared and fed on non-sterile protein-rich materials (as e.g. feather, hair and wool).

Further enrichment through dissection (optional): The larvae were decapitated under a stereoscopic microscope after which the gut (including gut content) was selected and pooled together from several animals DNA preparation: DNA preps were made from such composite gut materials using commercially available DNA kits. This high quality DNA material was used to prepare a genomic library.

RNA preparation: Total RNA preps were made from said composite gut material using commercially available RNA kits and protocols. The mRNA fraction was subsequently harvested. Based on this the corresponding cDNA prep was made. This was used to construct a cDNA library, representing the expressed proteins at the given time.

Screening of the genomic library enriched for DNA from those organisms specifically benefiting from the feeding conditions of the larvae under preparation: a plaque screening procedure was adapted to enzyme substrate holding plates, indicating which phages were holding an insert of a full functional gene encoding an enzyme with the protease activity of interest.

Screening of the cDNA library enriched for high expression of proteins useful to degrade the feed given to the larvae: the protocol for expression cloning, as given in H.Dalbøge, 1997 (FEMS Microbiology Reviews 21, 29–42).

Identified hits: Protease active clones could be identified by screening on substrate plates with AZCL-casein blue granules from MegaZyme. The protease hits could be further subdivided according to which types of protein bonds they specifically degrade.

Example 8

Enrichment of *Melolontha vulgaris* Larvae Gut for Plant Cell Wall Degrading Enzymes Materials: Larvae of *Melolontha vulgaris* (Coleoptera) were collected from Danish habitats (Zealand) where the soil is rich in a very varied composition of plant debris. The larvae of this species are free living in soil, feeding for up to 3 years on plant materials Enrichment procedure: The larvae were subsequently reared and fed non-sterile non-specified plant debris of a very broad taxonomic composition.

Further enrichment through dissection (optional): The larvae were decapitated under a stereoscopic microscope after which the guts (including gut content) were selected and pooled together from several animals.

DNA preparation: DNA preps were made from such composite gut material using commercially available DNA kits. This high quality DNA material was used to prepare a genomic library.

RNA preparation: Total RNA preps were made from said composite gut material using commercially available RNA kits and protocols. The mRNA fraction was subsequently harvested. Based on this, the corresponding CDNA prep was made. This was used to construct a cDNA library, representing the expressed proteins at the given time.

screening of the genomic library enriched for DNA from those organisms specifically benefiting from the feeding conditions of the larvae under preparation: a plaque screening procedure was adapted to enzyme substrate holding plates, indicating which phages were holding a (functional) gene insert encoding an enzyme with the plant cell wall degrading activity of interest.

Screening of the cDNA library enriched for high expression of proteins useful to degrade the feed given to the larvae: the protocol for expression cloning, as given in H.Dalbøge, 1997 (FEMS Microbiology Reviews 21, 29–42).

Identified hits: Numerous types of cell wall degrading enzymes could be identified by screening on the variety of Azur cross linked blue granule substrates available from MegaZyme.

Example 9
Enrichment of Agrotis Larvae Guts for Amylases

Materials: Larvae of Agrotis (Lepidoptera) were received from RVAU (Royal Veterinary and Agricultural University), Copenhagen (Professor Peter Esbjerg).

Enrichment procedure: The larvae were subsequently reared and fed non-sterile starch rich materials.

Further enrichment through dissection (optional) the larvae were decapitated under a stereoscopic microscope after which the guts (including gut content) were; selected and pooled together from several animals.

DNA preparation: DNA preps were made from such composite gut material using commercially available DNA kits. This high quality DNA material was used to prepare a genomic library.

RNA preparation: Total RNA preps were made from the composite gut material using commercially available RNA kits and protocols. The mRNA fraction was subsequently harvested. Based on this fraction the corresponding cDNA prep was made. This was used to construct a cDNA library, representing the expressed proteins at the given time.

Screening of the genomic library enriched for DNA from those organisms specifically benefitting from the feeding conditions of the larvae under preparation: a plaque screening procedure was adapted to enzyme substrate holding plates, indicating which phages were holding an insert of a functional gene, encoding an enzyme with a plant cell wall degrading activity of interest.

Screening of the cDNA library enriched for high expression of proteins useful to degrade the feed given to the larvae: the protocol for expression cloning, as given in H.Dalbøge, 1997 (FEMS Microbiology Reviews 21, 29–42).

Identified hits: The AZCL-amylose blue granule substrates were used for a plate screening of the yeast (and the plaque) colonies. High alkaline amylases could be found by overlaying the expression cloning yeast plates with glycine buffer, pH 10. The colonies which only developed the blue halo of diffusing blue colour around the granules after buffer treatment, were the clones in which a gene encoding an alkaline amylase had been inserted and was expressed.

Example 10

Enrichment of Cow Rumen Content for Cellulases, Proteases and Amylases

Materials: Samples were taken in a semianaerobic manner directly from a fistulated cow (at RVAU, Rørrendegård, T astrup, Denmark).

Enrichment procedure: The cow was in the weeks prior to the sampling fed material of specific composition e.g. hey to enrich for cellulase and other plant cell wall degrading enzymes, cereal grains to enrich for amylase activity and soy to enrich for protease activities.

Further enrichment through dissection (optional): Microscopic analysis was made on further dissected fractions, reflecting the various degrees of feed breakdown in the rumen.

DNA preparation: DNA preps were made from such composite rumen material using commercially available DNA kits. This high quality DNA material was used to prepare a genomic library.

RNA preparation: Total RNA preps were made from the composite rumen material using commercially available RNA kits and protocols. The mRNA fraction was subsequently harvested. Based on this the corresponding cDNA prep was made. This was used to construct a cDNA library, representing the expressed proteins at the given time.

Screening of the genomic library enriched for DNA from those organisms specifically benefitting from the feeding conditions of the larvae under preparation: a plaque screening procedure was adapted to be made on enzyme substrate holding plates, indicating which phages were holding an insert of a full functional gene, encoding an enzyme with the activity of interest.

Screening of the cDNA library enriched for high expression of proteins useful to degrade the feed given to the larvae: the protocol for expression cloning, as given in H.Dalbøge, 1997 (FEMS Microbiology Reviews 21, 29–42).

Identified hits: Several types of enzyme activities were found, e.g. more than 20 cellulase active clones were identified on HE Azur cross linked blue granule substrates from MegaZyme. Colony PCR was used to differentiate and group the hits. At least four different sized functional genes were hereby identified.

What is claimed is:

1. A method generating a gene library from an environmental pool of organisms isolated from soil, animal dung, insect gut, animal stomach, sea or lake water, waste water, sludge, or sediment, which gene library is enriched in DNA encoding a polypeptide with an activity of interest, which method comprises:
   a) subjecting the environmental pool of organisms to cultivation under conditions wherein the pool of organisms is enriched in organisms harbouring said DNA, thereby forming an enriched environmental pool of organisms, and
   b) preparing a gene library from the enriched environmental pool of organisms, wherein prior to said preparing there is no further purification of the enriched environmental pool of organisms.

2. The method of claim 1, wherein the conditions are culturing in a medium that contains a substrate for the polypeptide with an activity of interest encoded by said DNA.

3. The method of claim 2, wherein the substrate constitutes the carbon source and/or nitrogen source of the medium.

4. The method of claim 2, wherein the substrate comprises pectin, amylose, cellulose, galactose, xylose or arabinose or a combination thereof.

5. The method of claim 1, wherein the pool of organisms is enriched by one or more growth restrictions.

6. The method of claim 5, wherein the growth restrictions comprise pH and temperature.

7. The method of claim 5, wherein the growth restriction are pH 9–11 and temperature 50–70° C.

8. The method of claim 1, wherein the environmental pool of organisms is isolated from an animal stomach or an insect gut.

9. The method of claim 6, wherein the pool of organisms is isolated from a cow's rumen.

10. The method of claim 8, wherein the pool of organisms is isolated from the gut of an insect of the Isoptera, Lepidoptera, Coleoptera, or Diptera families.

11. The method of claim 10, wherein the pool of organisms is isolated from the gut of insects selected from the group consisting of Agrotis, *Neotermes castaneus, Tineola bisselliella*, and *Melolontha vulgaris*.

12. The method of claim 8, wherein prior to isolation, the pool of organisms is enriched by supplying feed to the animal or insect, which comprises a substrate for the polypeptide with an activity of interest.

13. The method of claim 1, wherein the gene library is enriched in DNA encoding an enzyme of interest.

14. The method of claim 13, wherein the enzyme of interest comprises a hydrolase, an coddoreductase, a transferase, a lyase or a ligase.

15. The method of claim 14, wherein the enzyme of interest comprises a protease, lipase, beta-galactosidase, lactase, polygalacturonase, beta-glucoamylase, esterase, hemicellulase, peroxidase, oxidase, laccase or glucose oxidase.

16. The method of claim 14, wherein the enzyme of interest is a pectinase, an amylase, a galactanase, an arabinase, a xylanase, or a cellulase.

17. The method of claim 1, wherein the environmental pool of organisms comprises microorganisms.

18. The method of claim 17, wherein the environmental pool of organisms comprises enzyme producing microorganisms.

19. The method of claim 17, wherein the microorganisms comprise Eubacteria, Archaebacteria, fungi, algae and/or protozoa.

20. A method of identifying a DNA sequence encoding a polypeptide of interest from an environmental pool of organisms isolated from soil, animal dung, insect dung, insect gut, animal stomach, sea or lake water, waste water, sludge, or sediment, which method comprises:

a) subjecting the environmental pool of organisms to cultivation under conditions wherein the pool of organisms is enriched in organisms harbouring said DNA, sequence thereby forming an enriched environmental pool of organisms;

b) producing gene libraries from the enriched environmental pool of organisms prior to said producing there is no further purification of the enriched environmental pool of organisms, c) screening the libraries of step b) to identify a DNA sequence encoding the polypeptide of interest.

21. A method of claim 20, wherein the polypeptide of interest encodes an enzyme.

22. The method of claim 20, wherein the gene libraries are screened in step c) for an active enzyme.

23. The method of claim 20, wherein the polypeptide of interest encodes a pectinase, amylase, galactanase, arabinase, xylanase or cellulase.

\* \* \* \* \*